United States Patent
Yokosawa et al.

(10) Patent No.: US 7,242,309 B2
(45) Date of Patent: Jul. 10, 2007

(54) GAS DETECTION SYSTEM

(75) Inventors: Koichi Yokosawa, Kokubunji (JP); Sadaki Nakano, Kokubunji (JP); Yasushi Goto, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 214 days.

(21) Appl. No.: 11/070,460

(22) Filed: Mar. 3, 2005

(65) Prior Publication Data

US 2006/0114113 A1 Jun. 1, 2006

(30) Foreign Application Priority Data

Nov. 26, 2004 (JP) ............................. 2004-341897

(51) Int. Cl.
G08B 17/10 (2006.01)
(52) U.S. Cl. .................... 340/632; 340/628; 73/1.06
(58) Field of Classification Search ........ 340/628–630, 340/632–634; 73/1.06
See application file for complete search history.

(56) References Cited

U.S. PATENT DOCUMENTS 4,390,869 A * 6/1983 Christen et al. ............ 340/632

(Continued)

FOREIGN PATENT DOCUMENTS

JP 6-60276 8/1992

(Continued)

OTHER PUBLICATIONS

I. Lundstrom et al., "Catalytic Metals and Field-Effect Devices—A Useful Combination", Sensors and Actuators, vol. B1, (1990) pp. 15-20.

(Continued)

Primary Examiner—Jeffery Hofsass
Assistant Examiner—Anne V. Lai
(74) Attorney, Agent, or Firm—Reed Smith LLP; Stanley P. Fisher, Esq.; Juan Carlos A. Marquez, Esq.

(57) ABSTRACT

A gas detection system capable of suppressing the power consumption of the system using gas sensors required for heating for measurement at high accuracy, comprising a server and a plurality of gas sensors connected by way of wireless communication with the server, in which each of the gas sensors is provided with a heater, a controller for controlling the ON-OFF for the power supply to the heater and a comparator for comparing the detected gas concentration with a predetermined threshold value. In the gas detection system, electric power is not usually supplied to the heater in each of the gas sensors and the gas sensor measures the gas concentration at a low accuracy and always compares it with the threshold value. In a case where the gas concentration exceeds the threshold value in one of the gas sensors, it turns the heater of its own to ON thereby switching the measurement to that at high accuracy and turns the heater to OFF upon completing the measurement. At the same time, it informs the detection for the excess of threshold value to the server and the server lowers the threshold value of the gas sensors in the vicinity of the gas sensor that has informed the detection for the excess of threshold value to make the monitoring level severer.

5 Claims, 9 Drawing Sheets

U.S. PATENT DOCUMENTS

| | | | |
|---|---|---|---|
| 6,166,647 A * | 12/2000 | Wong | 340/628 |
| 6,279,377 B1 * | 8/2001 | Cao | 73/23.31 |
| 6,437,698 B1 * | 8/2002 | Byrne et al. | 340/630 |
| 6,856,252 B2 * | 2/2005 | Pfefferseder et al. | 340/628 |
| 2003/0174056 A1 * | 9/2003 | Harshaw | 340/522 |
| 2005/0155405 A1 * | 7/2005 | Sasaki et al. | 73/1.06 |

FOREIGN PATENT DOCUMENTS

| | | |
|---|---|---|
| JP | 6-301873 | 4/1993 |
| JP | 7-272166 | 3/1994 |
| JP | 07-272166 | 3/1994 |
| JP | 8-249565 | 3/1995 |
| JP | 2001-93059 | 9/1999 |
| JP | 2002-357576 | 5/2001 |
| JP | 2003-141658 | 6/2002 |

OTHER PUBLICATIONS

Woosuck Shin et al., "Thermoelectric Thick-Film Hydrogen Gas Sensor Operating at Room Temperature", Japanese Journal of Applied Physics, vol. 40 (Nov. 15, 2001), pp. L1232-L1234.

Eric Chanie et al, "Real Time Environmental Monitoring with Wireless Distributed Sensor Array System", The 10$^{th}$ International Meeting on Chemical Sensors, Technical Digest, Chemical Sensors, vol. 20, Supplement B (2004), pp. 94-95.

* cited by examiner

GAS DETECTION SYSTEM

CLAIM OF PRIORITY

The present application claims priority from Japanese application JP-2004-341897 filed on Nov. 26, 2004, the content of which is hereby incorporated by reference into this application.

FIELD OF THE INVENTION

The present invention relates to a system for detecting the change of the gas concentration and, more in particular, it relates to a system control technique suitable to a detection system of monitoring the distribution of gas concentration by arranging a plurality of gas sensors.

BACKGROUND OF THE INVENTION

Gas sensors include various types. For flammable gas sensors, for example, contact combustion type, semiconductor type, heat conduction type, infrared absorption, etc. have been known as described in JIS M 7626 "Stational Type Combustible Gas Detection Alarm". Further, as a system of using thin films or thick films, an FET system (system of depositing gas sensing membrane on a gate electrode of FET and reading the change of the gate potential caused by a target gas) by using the FET as described in the Journal of Sensors and Actuators, Vol. B1, pp 15 to 20, or a thermoelectric system (system of reading the temperature rise of a thermoelectric conversion membrane by a target gas as a voltage) as described in Japanese Journal of Applied Physics, Vol. 40, pp L1232 to 1234 has been proposed.

While the examples described above concern the single sensor elements per se, a method of detecting a hydrogen gas in a wide range of concentration by using plural sensors of different output linear regions relative to the concentrations (JP-A No. 2002-357576) has been laid-open as an example of using plural sensors.

It has been expected that detection systems of measuring not only the gas concentration at specified positions but also measuring the distribution of the gas concentration over entire facilities and consequence monitoring for the leakage diffusion and determining the leaked position will be popularized in the feature. Since hydrogen filling stations for supplying hydrogen gas to fuel cell vehicles are built in city areas and required high safety, they are typical example of facilities requiring such detection systems.

A technique of connecting plural gas sensors by way of wireless communication and monitoring the concentration distribution of a gas has been described, for example, in the 10th International Meeting on Chemical Sensors, Technical Digest, pp 94 to 95. This example proposes to hybridize several kinds of sensors such as electrochemical sensors or optical ionization sensors and construct a VOC monitoring system for odors in waste water treating plants, dust disposing plants, livestock barns, clean rooms, etc.

[Patent Document 1]
Japanese Patent Laid-Open No. 2002-357576

[Non-Patent Document 1]
Journal of Sensors and Actuators, vol. B1, pp 15 to 20

[Non-Patent Document 2]
Japanese Journal of Applied Physics, vol. 40, pp L1232 to L1234.

[Non-Patent Document 3]
The 10th International Meeting on Chemical Sensors, Technical Digest, PP 94 to 95

SUMMARY OF THE INVENTION

In a case of measuring the distribution of gas concentration in a wide area by arranging from several tens to several hundreds of gas sensors, by constituting a sensor node so as to incorporate gas sensors, wireless communication function, and power supply, laying of wirings is not necessary to facilitate the arrangement of sensor nodes. One of important subjects in the sensor nodes incorporated with the power supply is to decrease power consumption.

Decrease of the power consumption includes that of the power consumption of wireless communication and that of the power consumption of gas sensors per se. Referring to the power consumption of the gas sensors per se, in a case where it is necessary to use the gas sensor under heating in order to maintain the high measuring accuracy of the gas sensor, the power consumption in a heater for heating the gas sensor is extremely high. As described above, while the gas sensors are based on several methods, since the chemical reactions are effectuated by temperature, particularly, in gas sensors of utilizing electrochemical reactions such as in the semiconductor system, FET system or thermoelectric system, control for the temperature is important. Also for other systems, the temperature of the gas sensors are often kept high (about 100° C. to 150° C.) in view of the requirement of increasing the response speed and suppressing the measuring error due to temperature.

That is, in most of gas sensors, the accuracy of the gas sensor is determined depending on the presence or absence of heating for the gas sensor and measurement, at a room temperature, can be conducted only at a low accuracy also with the effect of atmospheric temperature or humidity. On the other hand, when the temperature is controlled, for example, to about 100° C., measurement at high accuracy is possible. Accordingly, a constitution of keeping the gas sensor at a high temperature by disposing a thin film heater near the gas sensor has been proposed, for example, as in Japanese Patent No. 2848818.

Heating of the gas sensor increases the power consumption and also accelerate deterioration of the gas sensor. Particularly in a case, for example, of using a dry cell as a power supply for the sensor node, if the power consumption of the heater that heats the gas sensor is large, it can not cope with the detection for gas leakage over a long period of time. The present invention intends to attain compatibility between the requirement of conducting measurement at high accuracy and suppressing of the power consumption as much as possible.

Generally, heating by the heater consumes much more electric power compared with that in the driving circuit for the gas sensor. For suppressing the power consumption, it is most effective to minimize the time of power supply time to the heater. In a sensor system comprising plural sensor nodes and a server associated therewith, the subject of conducting measurement for gas concentration at high accuracy while suppressing the consumption of the power as low as possible can be solved by a system constitution of supplying power only to the required minimum number of gas sensors only for the required minimum time, for example, upon calibration of gas sensors, periodical measurement, or gas leakage detection in the sensor node.

More specifically, in each of the sensor nodes, a heater, a controller that controls ON-OFF of power supply to the heater and a comparator for comparing the concentration of the detected gas with a predetermined threshold value are provided. The outline for the flow of the system control is to be described below.

Usually, electric power is not supplied to the heaters for all of the gas sensors and gas sensors measure the gas concentration at low accuracy. Further, a threshold value relative to the measured value of the gas sensor is set to a high value, and them the monitoring level is moderate (that is, monitoring at moderate level). In a case where the measured value of gas sensor exceeds a threshold value in one of the sensor nodes, the sensor node informs the server that the measured value exceeds the threshold value and, at the same time, starts power supply to the heater of its own to switch the measurement to that at high accuracy. The measured data at high accuracy is informed to the server.

Upon receiving the information that the measured value has exceeded the threshold value, the server sends a control signal to sensor nodes arranged at the periphery of the sensor node that has informed the excess of the threshold value so as to lower the threshold value of the gas sensor and switch the monitor level to a rigorous level (that is, monitoring at rigorous level).

The sensor node receiving the control signal lowers the threshold value and switches the monitor level to a rigorous level monitoring. That is, it tends to exceed the threshold value even when the measured value for the gas concentration is still low.

In a case where the server can judge the state as not abnormal based on the data of the measurement at high accuracy from the sensor node that at first informed that the threshold value was exceeded and the result of judgment whether it is correct or erroneous by the sensor node per se based on the measurement at high accuracy of the sensor node, the server sends a control signal to increase the threshold value of the gas sensor to an original value to the sensor node that sent a control signal so as to lower the threshold value of the gas sensor, thereby returning the node to the initial state.

In view of the system operation, in a case of requiring measurement at high accuracy such as upon calibration of the gas sensor in each of the sensor nodes, or periodical measurement, the server sends a control signal so as to supply power to the heater for the sensor node only for the period of time that requires measurement at high accuracy and controls such that the power is supplied to the heater in the sensor node.

According to the system control as described above, power supply to the heater can be restricted only to the required minimum period for the measurement at high accuracy and the power consumption can be suppressed.

DESCRIPTION OF THE PREFERRED EMBODIMENT

Figure 1:
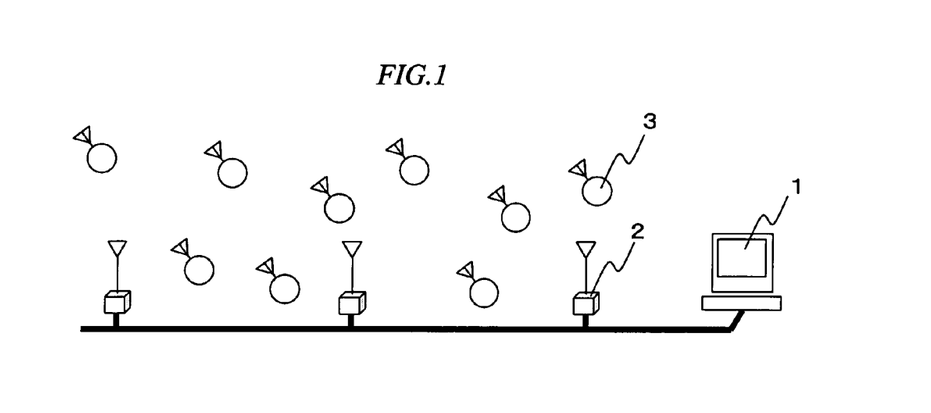
FIG. 1 is a conceptional view for the system constitution in the present invention.
Figure 2:
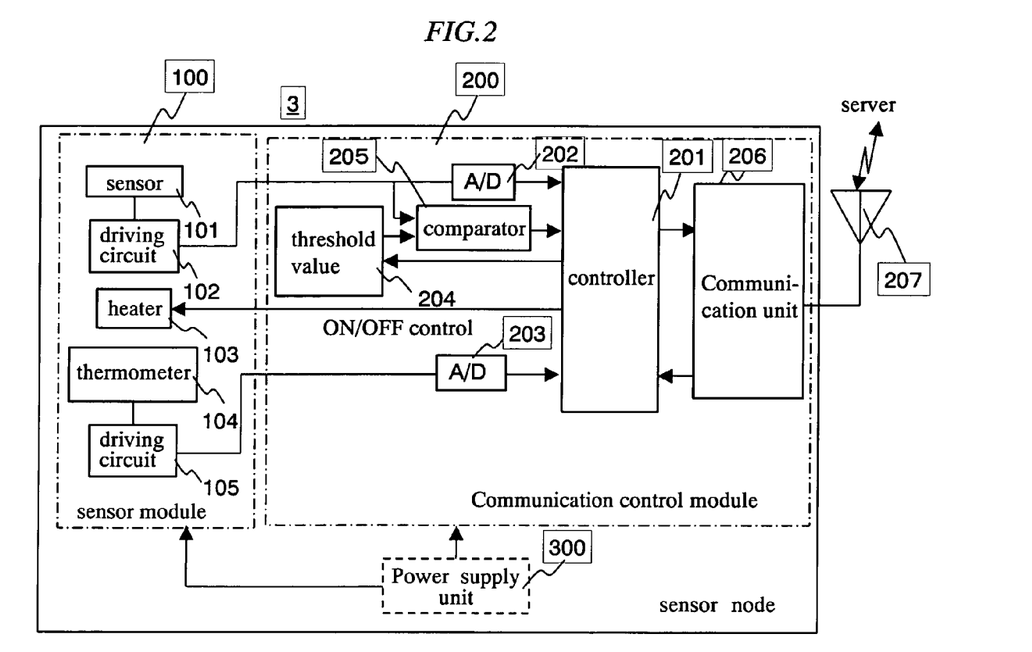
FIG. 2 is a block diagram showing an example of a sensor node in the invention.
Figure 3:
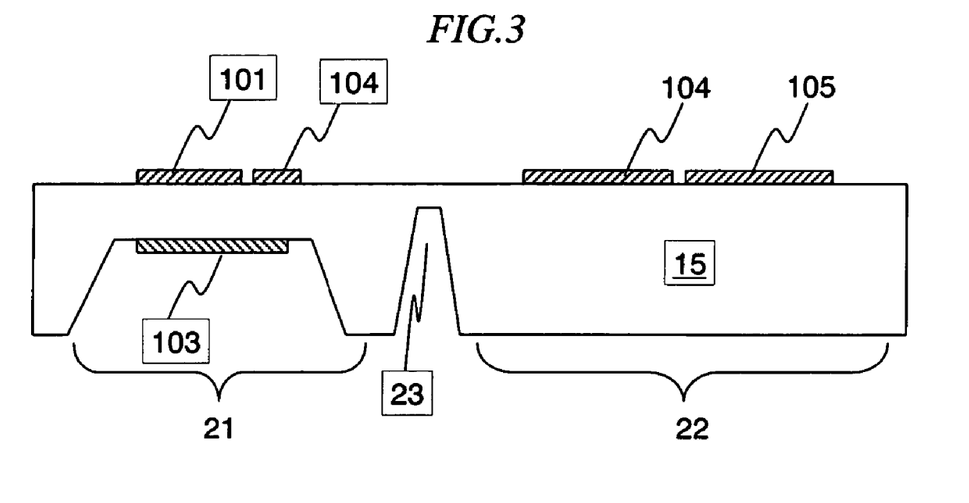
FIG. 3 is a view showing an example of the constitution of a sensor module 100 as cross section.

An example of the constituent factors of the present invention is to be shown at first with reference to FIG. 1 to FIG. 3.

FIG. 1 is a conceptional view for the system constitution of the present invention. Sensor nodes each having a gas sensing function and a wireless communication function are provided in plurality. On the other hand, access points 2 connected with a server 1 are located at plural positions and the respective sensor nodes 3 are in communication by way of wireless communication to the server 1 through the access points 2. In the following example, explanation is to be made assuming that each of the sensor nodes 3 is in communication by way of the wireless communication with the server 1 in accordance with the configuration shown in FIG. 1 but the effect of power saving can also be obtained by the same flow in a case of wired communication. Further, for the simplicity of the explanation, description is to be made to an example of leakage of deleterious gas (noxious gas, flammable gas, etc.) all cases regarding detection of abnormal values for the gas concentration such as abnormal generation of deleterious gas, abnormal lowering of the concentration of necessary gases such as an oxygen or process gas can be coped with an identical flow.

FIG. 2 is a block diagram showing an embodiment of a sensor node of the invention.

A sensor node 3 comprises a sensor module 100, a communication control module 200 and a power supply system 300. The sensor module 100 is constituted with a gas sensor 101, a driving circuit 102 for the gas sensor, a heater 103, a temperature meter 104 and a driving circuit 105 for the temperature meter.

The communication control module 200 comprises a communication system 206 and a controller (microcomputer) 201. The communication system 206 is connected to an antenna 207. The outputs from the gas sensor 101 and the temperature meter 104 are introduced to the controller 201 by way of A/D converters 202 and 203. Further, a threshold value setting circuit 204 is provided. A threshold value is set for the threshold value setting circuit 204 by the controller 201. A comparator 205 compares the output from the gas sensor 101 with a threshold value of the threshold value setting circuit 204 and, in a case where the output from the gas sensor 101 exceeds the threshold value, sends a signal to the controller 201, and the controller 201 sends an ON signal to the heater 103. The controller 201 is programmed such that it sends the ON signal to the heater 103, and then sends an OFF signal to the heater 103 automatically at a timing the gas sensor is enabled for predetermined measurement at high accuracy and has completed acquisition of the data for the high accuracy measurement. Then, the output from the gas sensor 101 and the output from the temperature meter 103 are sent to the server 1.

On the other hand, upon receiving a control signal of lowering the threshold value for the gas sensor sent from the server 1 and switching a monitor level to a rigorous level monitoring, the controller 201 sets a lower setting value to the threshold value setting circuit 204. Further, when the server 1 sends a return instruction for returning the threshold value of the gas sensor to an original value, it sets a higher original setting value for the threshold value setting circuit 204.

The power supply system 300 supplies electric power to each of constituent elements and the driving circuit of the sensor module 100 and the communication control module 200.

In this embodiment, while the sensor module 100 and the communication control module 200 are constituted as described above for the sake of convenience, the A/D converters 202 and 203 may also be constituted on the sensor module 100, or the functions of the comparator 205 and the threshold value setting circuit 204 may be incorporated in the controller 201. In the same manner, the constitution and the arrangement for the constituent elements on each module are not limited as described above.

FIG. 3 is a view showing a constitutional example of the sensor module 100 in a cross section. A gas sensor 101, a temperature meter 104, a heater 104, and driving circuits 104 and 105 are integrated on one sheet of a silicon substrate 15. In the sensor portion 21 to be controlled for the temperature by heating (gas sensor 101, temperature meter 104, heater 104), the thickness of the substrate 15 is reduced by etching at the back surface such that the heat capacity is decreased. Further, for thermally separating the sensor portion 21 and the driving circuit portion 22, a moat 23 is dug to the back surface of the substrate. While the constitution of FIG. 3 has an advantage that the sensor module can be decreased in the size to facilitate heating for the gas sensor 101, this is not always necessary for obtaining the effect of the invention and, for example, the heater 103 and the driving circuit 104 and 105 may be constituted with electronic circuits parts, etc. and may be integrated with the sensor portion 21.

Examples for the flow of the system control according to the invention are to be described with reference to FIG. 4A to FIG. 7.

Figure 4A:
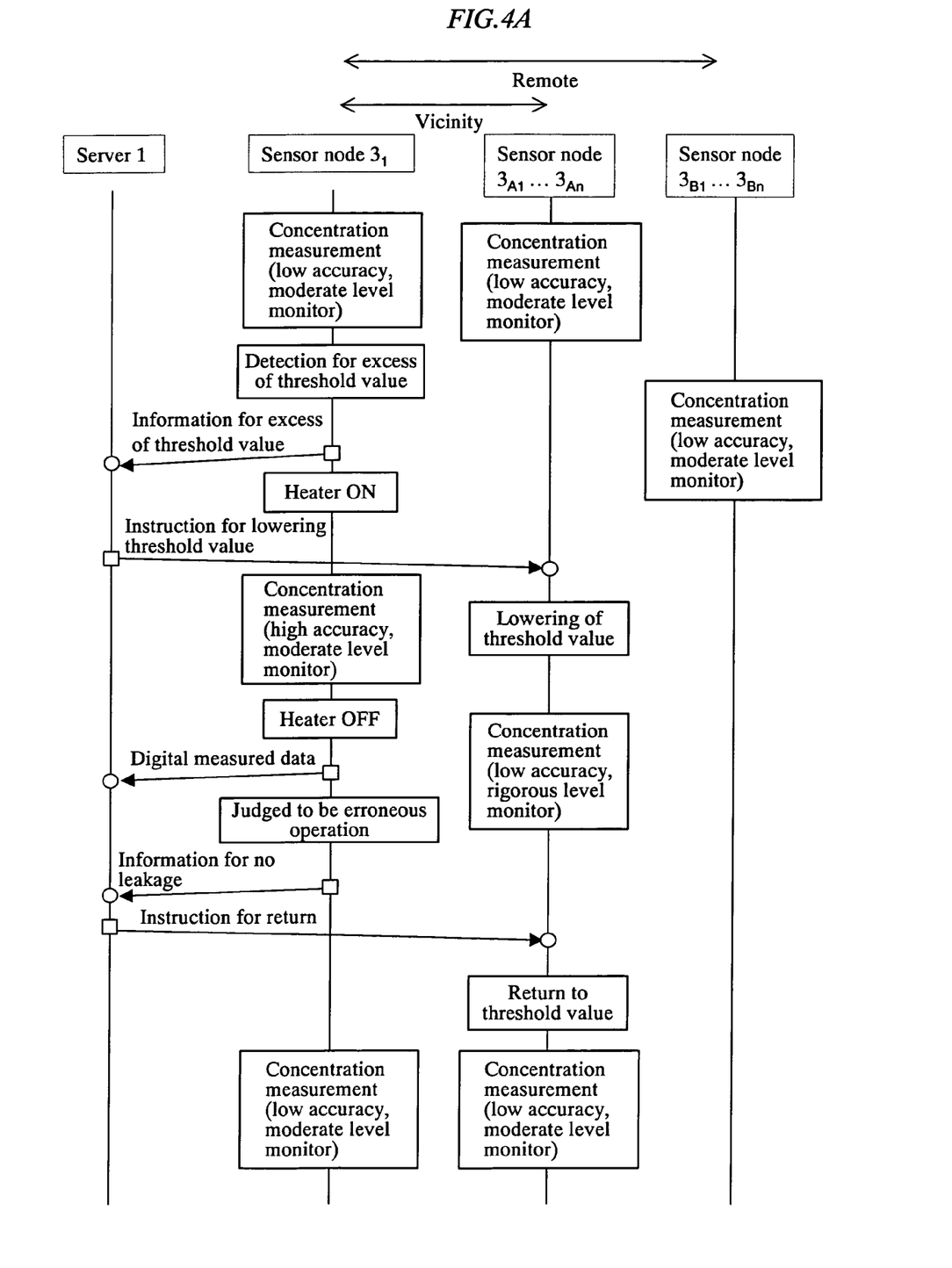
FIG. 4A is a view showing an example for the operation of a server 1 and a sensor node and a state of communication between them.
Figure 5:
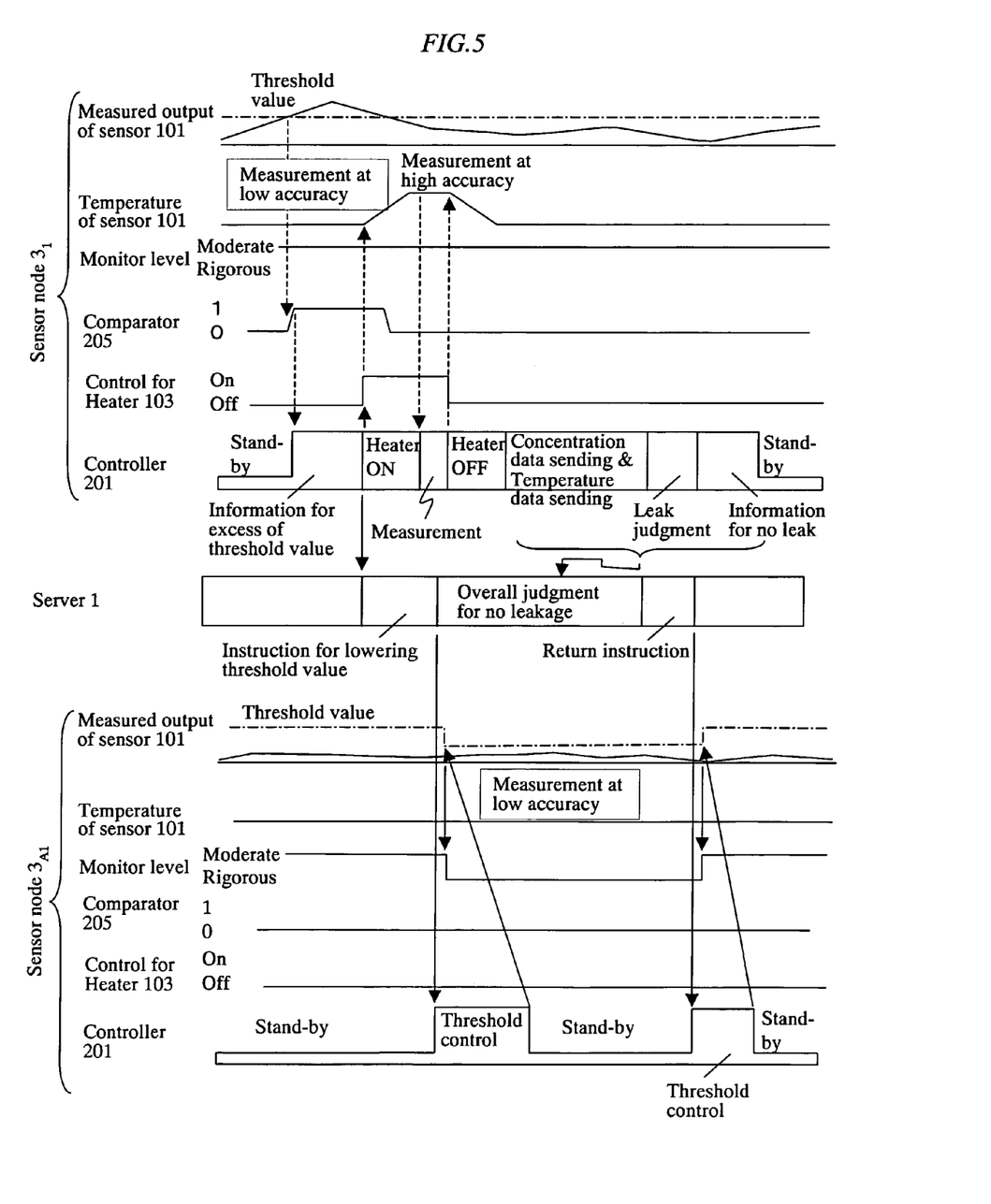
FIG. 5 is a view showing the operation and the state of communication in FIG. 4A in the form of a time chart.

FIG. 4A is a view showing an example for the operation of the server 1 and sensor nodes and communication state between them. FIG. 4A is a view showing the operation of a sensor node $3_1$, a sever 1, sensor nodes $3_{A1}$ to $3_{An}$ in the vicinity of the sensor node $3_1$ and sensor nodes $3_{B1}$ to $3_{Bm}$ remote from the sensor node $3_1$ and the communication state thereof in a case where one sensor node $3_1$ detects that the gas sensor output exceeds a threshold value and when this detection is an erroneous operation. Further, FIG. 5 is a view showing the operation and the communication state in FIG. 4A in the form of a time chart.

Usually, the sensor node 3 conducts measurement in a stationary state, that is, at low accuracy and moderate level monitoring. That is, as shown in FIG. 5, the heater 103 is not supplied with power in each sensor node 3 in order to prevent power consumption, in which the temperature of the gas sensor 101 is low and the controller 201 is in a stand-by state. The measured value at low accuracy of the gas sensor is always compared with the threshold value.

Now, assuming that the threshold value of the measured concentration data exceeds in the sensor node $3_1$, a comparator 205 generates a trigger to actuate the controller 201. The sensor node $3_1$ informs excess of the threshold value to the server 1 and, at the same time, turns the heater 103 to ON.

Upon receiving information for the excess of the threshold value from any one of the sensor nodes 3, the server 1 instructs to lower the setting for the threshold value to the sensor node in the vicinity of the server 1. Decision of one of the sensor nodes 3 to be in the vicinity relative to an optional sensor node 3 may be conduct by previously determining in view of the entire arrangements of the sensor nodes and registration thereof in the server 1. For example, it is practical to register a sensor node to which a gas reaches within about 30 sec based on the calculation from the diffusion speed of a targeted gas as an object of measurement to be a sensor node in the vicinity. In the example of FIG. 4A, the instruction for lowering the threshold value is sent to sensor node $3_{A1}$ to $3_{An}$ which are determined to be in the vicinity of the sensor node $3_1$.

Upon receiving the information for the excess of threshold value from the sensor node $3_1$, the server 1 lowers the threshold value for the sensor node $3_{A1}$ to $3_{An}$ in the vicinity and switches the monitor level to a rigorous level monitoring, so that abnormality can be found rapidly.

On the other hand, since the heater 103 is turned ON in the sensor node $3_1$, the temperature of the gas sensor 101 is increased to enable measurement at high accuracy. For making it possible to confirm that the gas sensor 101 has reached a predetermined temperature, A/D conversion data for the temperature data is taken together with the A/D conversion data for the gas sensor output into the controller 201. The controller 201, upon completion of necessary measurement, turns the heater 103 to OFF and transfers the measured data by way of the communication system 206 to the server 1.

At the same time, from the result of the gas concentration measured at high accuracy, the controller 201 judges whether this can be considered to be an actual leakage or not. Several methods may be considered for the judgment of the leakage. Most simply, a standard concentration value may be previously set to the controller 201, and the measured value and the standard value may be compared. In addition, there is a method of judging the leakage in a case where the change with time of the measured value exceeds a predetermined value. In a case where the controller 201 judges that this is not leakage, the controller 201 informs no leakage to the server 1.

On the other hand, the sensor nodes $3_{A1}$ to $3_{An}$ in the vicinity whose threshold value was lowered in accordance with the instruction of the server 1 monitor at high level but unless the measured value of the gas sensor 101 of the sensor nodes $3_{A1}$ to $3_{An}$ exceeds the lowered threshold value, they only continue measurement at low accuracy. In a case where the measured value of the gas sensor 101 in the sensor node $3_A$ in any one of the sensor nodes $3_{A1}$ to $3_{An}$ exceeds the lowered threshold value, like in the case for the sensor node $3_1$, the controller turns the heater 103 to ON, conduct measurement at high accuracy, turns the heater 103 to OFF and then sends the data after measurement at high accuracy to the server 1 and judges whether this is to be actually considered as leakage from the result of the gas concentration measured at high accuracy. In a case where the controller 201 judges that this is not leakage, the controller 201 informs no leakage to the server 1. The process described above is shown in the upper stage of FIG. 5.

Server 1 judges the absence or presence of leakage based on the information for no leakage from the sensor node $3_1$ and, if necessary, based on the measured data at high accuracy informed from the sensor node $3_1$. When the server 1 collectively judges no leakage, it judges that the information for the excess of threshold value from the sensor node $3_1$ is erroneous information and sends an instruction for returning the threshold value to the sensor nodes $3_{A1}$ to $3_{An}$ in the vicinity. In response to the instruction, the sensor nodes $3_{A1}$ to $3_{An}$ return the threshold value to the original high value and return to the moderate level monitoring. No particular operation is conducted for the remote sensor nodes $3_{B1}$ to $3_{Bm}$. The progress described above is shown in the lower stage of FIG. 5.

In the usual state, since all the gas sensors conduct measurement at low accuracy, it may be considered that the erroneous information as described above may occur. Also in such erroneous information, according to this embodiment, power supply to the heater 103 is restricted only to the sensor node that at first detected the excess of threshold value and the power consumption can be suppressed. As has been described previously, although any one of the sensor nodes $3_{A1}$ to $3_{An}$ the threshold value of which was lowered and which was switch to the severe level monitoring in response to the instruction for the lowering of the threshold value by server 1, detection for the excess of threshold value may also occur to possibly supply power for the heater of its own, the number of sensor nodes that supply electric power to the heater is minimized.

Naturally, in a case where a sufficient electric power is available, for example, in a case of using a battery of large capacity for the sensor node 3, electric power may be supplied to all of the sensor nodes $3_{A1}$ to $3_{An}$ or all the sensor nodes also including the remote sensor nodes in accordance with the information for the excess of threshold value from the sensor node to conduct measurement at high accuracy. Also in this case, the time requiring electric power for the controller or the heater is limited and power consumption can be suppressed greatly.

Figure 4B:
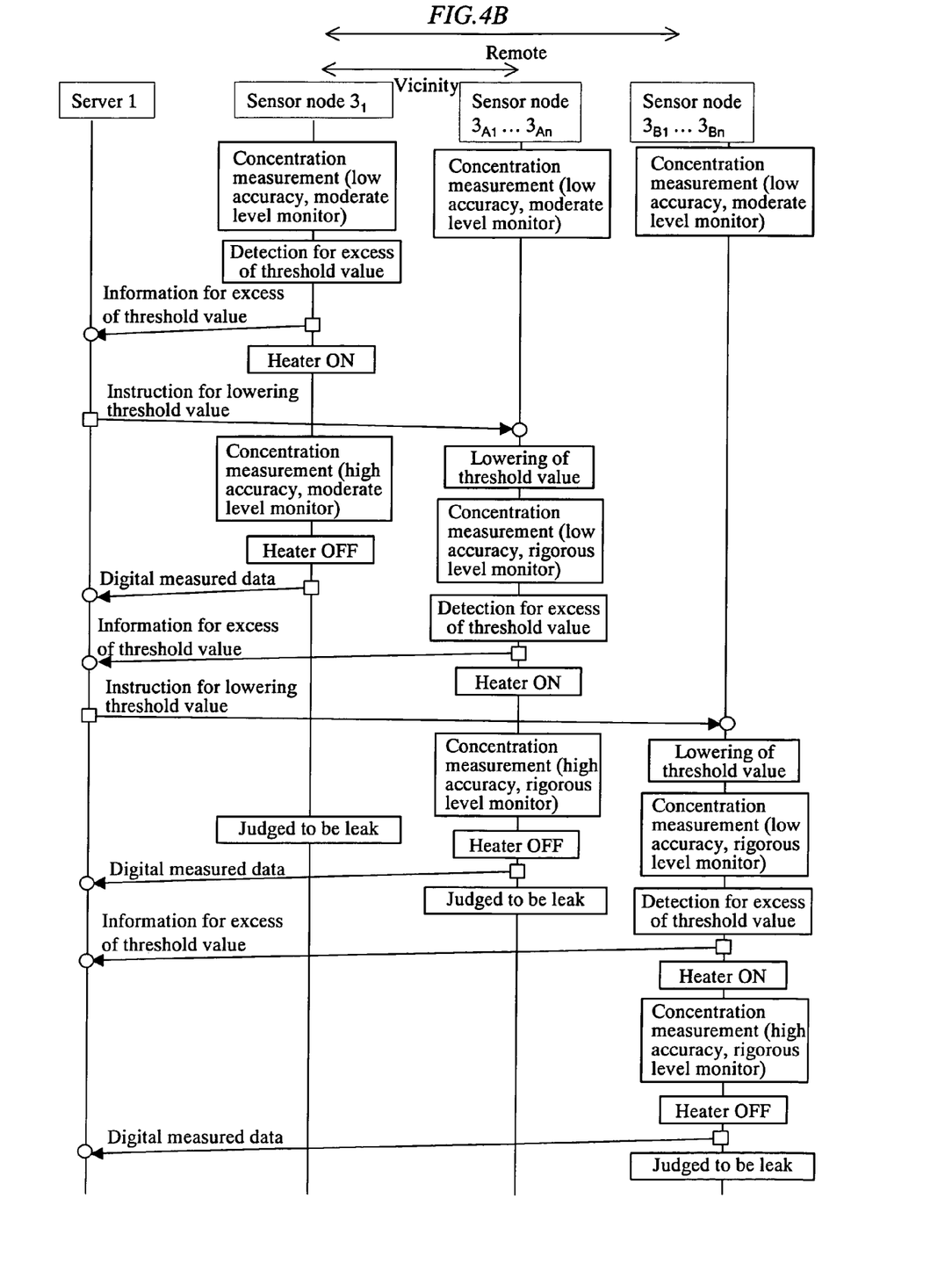
FIG. 4B is a view showing another example for the operation of a server 1 and a sensor node and a state of communication between them.

FIG. 4B is a view showing another example of the operation of the server 1 and the sensor nodes and communication state between them. FIG. 4B is a view showing the operation and the communication states for the sensor node $3_1$, the server 1, the sensor nodes $3_{A1}$ to $3_{An}$ in the vicinity of the sensor node $3_1$ and the sensor nodes $3_{B1}$ to $3_{Bm}$ remote from the sensor node $3_1$ in a case where one sensor node $3_1$ detects that the sensor output exceeds the threshold value.

At first, the process from the detection of the excess of threshold value in the measured data in the sensor node $3_1$ and information for the excess of threshold value to the server 1 till the turning ON of the heater 101 of its own, measurement at high accuracy and turning OFF of the heater 101 in a state where the measurement has been completed and sending of the measured data at high accuracy to the server is identical with the case of erroneous information explained with respect to the FIG. 4A. When the controller 201 judges leakage by the method as described for FIG. 4A, the sensor node $3_1$ does not inform no leakage different from the case of FIG. 4A. Further, as a result that the heater 101 is turned OFF, the sensor node $3_1$ once returns to the monitoring state at low accuracy and moderate level, since the excess of threshold value is detected again, the process described above is repeated but the indication therefor is omitted for avoiding the complexity of the drawing.

On the other hand, in response to the information for the excess of threshold value of the measured concentration data from the sensor node $3_1$, the server 1 lowers the threshold value of the sensor nodes $3_{A1}$ to $3_{An}$ in the vicinity to switch the same to the rigorous level monitoring. In FIG. 4B, since leakage occurs actually, excess of the threshold value for the measured concentration data is detected more rapidly in the sensor nodes $3_{A1}$ to $3_{An}$ in the vicinity switched to the severe level monitoring. Detection for the excess of threshold value is informed to the server 1 also in this case. Successively, also the sensor nodes $3_{A1}$ to $3_{An}$ in the vicinity start measurement at high accuracy by turning the heater 103 to ON, then the heater 101 is turned OFF when necessary measured data are obtained and, successively, the measured concentration data is sent to the sever 1. Further, the controller 201 judges leakage based on the data of its own.

In response to the information for the excess of threshold values of the sensor nodes $3_{A1}$ to $3_{An}$ in the vicinity, the server 1 further instructs lowering of the threshold value to the remote sensor nodes $3_{B1}$ to $3_{Bm}$. As a result, the remote sensor nodes $3_{B1}$ to $3_{Bm}$ operate in the same manner as the sensor nodes $3_{A1}$ to $3_{An}$ in the vicinity instructed for the lowering of the threshold value.

As described above, the sensor node 3 located in the region where leakage occures (all the sensor nodes in a case where leakage occurs over a wide region) conducts measurement at high accuracy by turning ON of the heater only for short time and the data of the result is transferred to the server 1. Based on the data recorded in the server 1, it is possible to recognize the diffusion state of the leaked gas, as well as estimate the position of leakage to take adequate action on real time.

Figure 6:
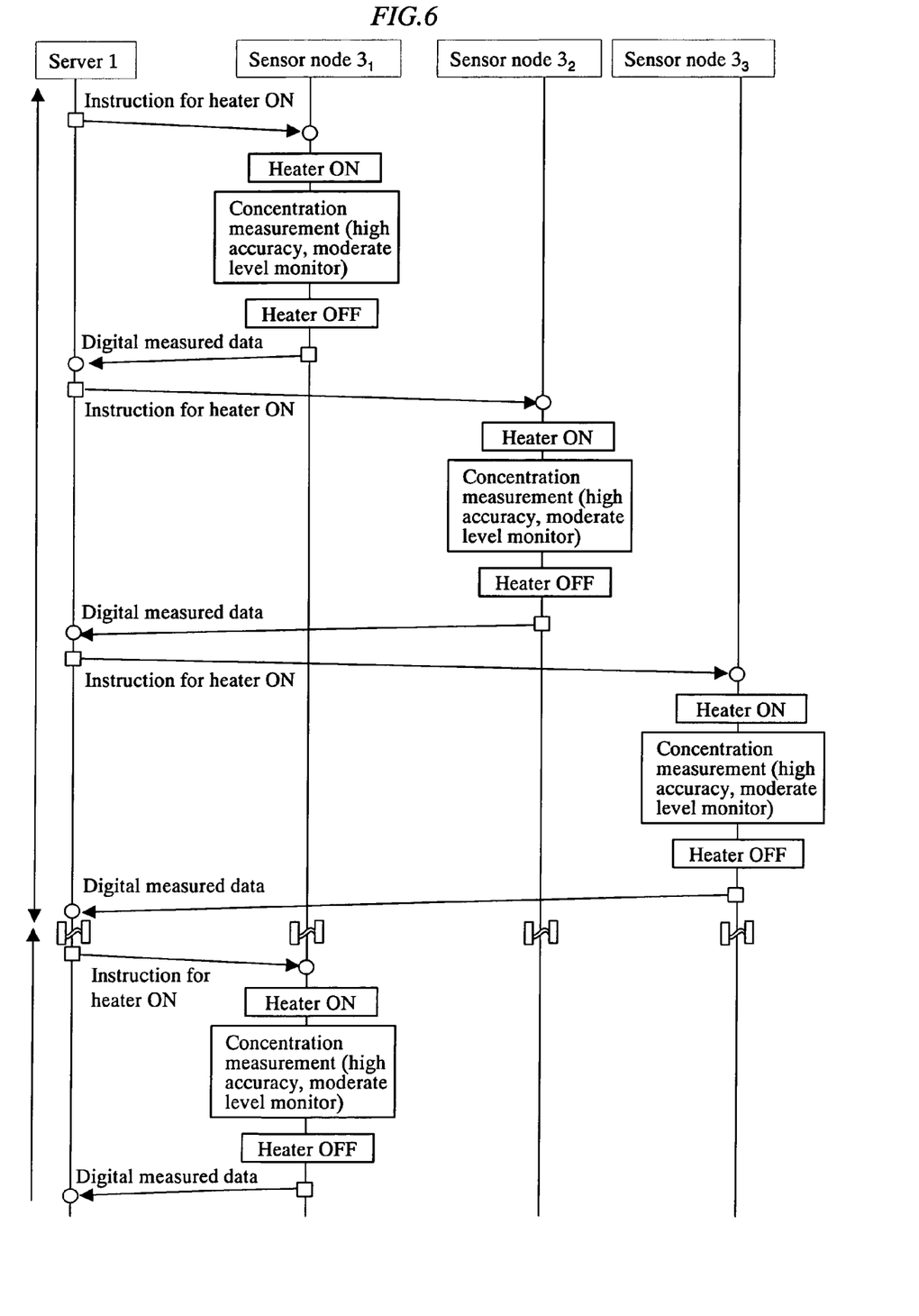
FIG. 6 is a view for explaining the flow during periodical measurement.

FIG. 6 is a view explaining the flow in the periodical measurement. The periodical measurement is a procedure of conducting measurement at high accuracy for all gas sensors at a predetermined time interval (for example, on every one hour), confirming no leakage and storing recording for the measured concentration data. In the periodical measurement, the instruction for turning the heater to ON is sent from the server 1 sequentially as each of the sensor node $3_1$, sensor node $3_2$, sensor node $3_3$ . . . on every predetermined time to collect measured at high accuracy for the gas concentration. Also in this case, the sensor node 3 receiving the instruction for the turning ON of the heater, conducts measurement at high accuracy in a state where the gas sensor 101 reaches a predetermined temperature and then automatically turns OFF the heater 103. Then, the measured data is sent to the server 1. This can minimize the power consumption in the sensor node 3.

Figure 7:
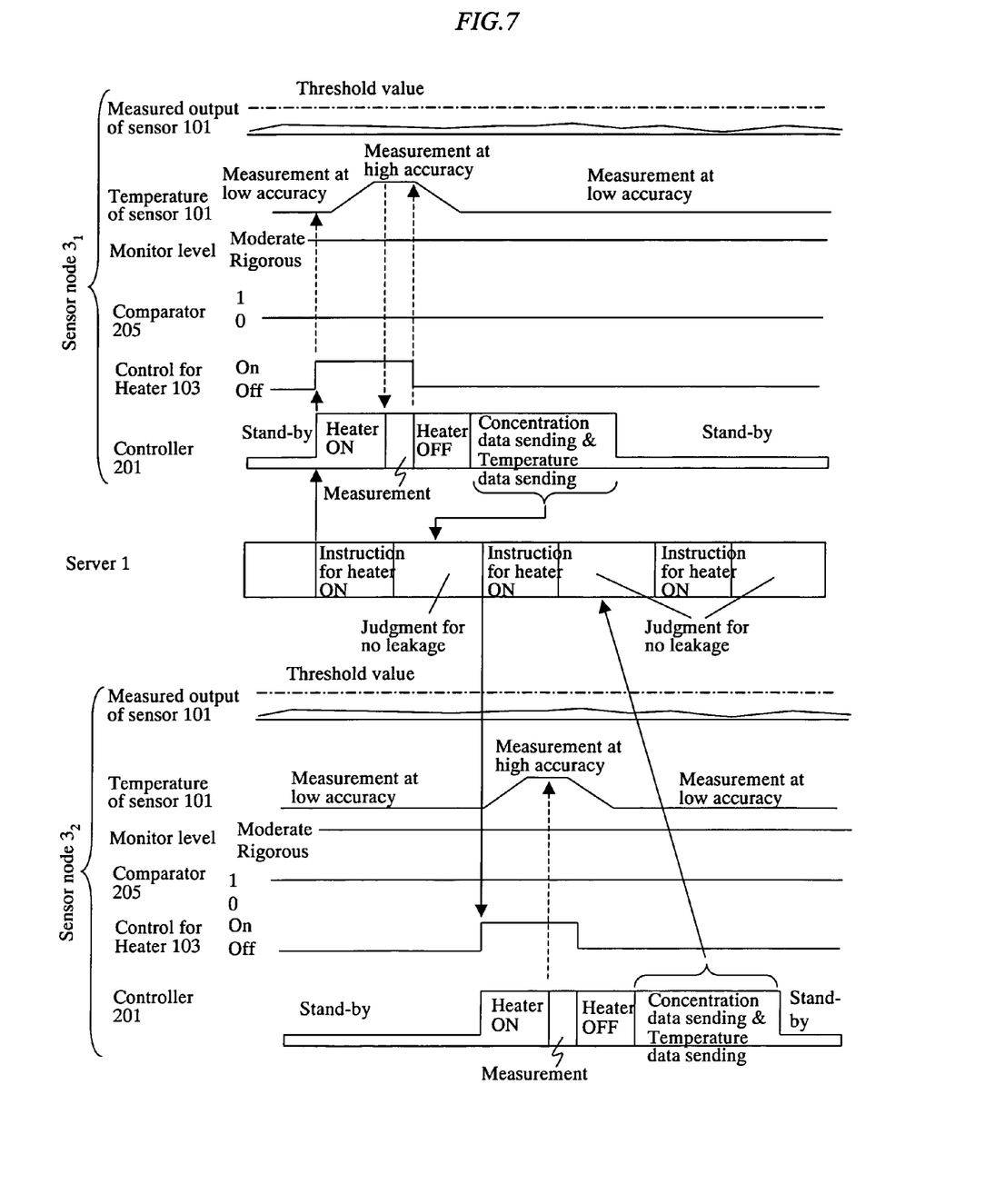
FIG. 7 is a time chart for explaining the operation of the server 1 and the sensor node 3 during periodical measurement shown in FIG. 6.

FIG. 7 is a time chart for explaining the operation of the server 1 and the sensor node 3 in the periodical measurement. When the server 1 sends an instruction of turning the heater to ON to the sensor node $3_1$, the sensor node $3_1$ turns the heater 103 to ON and after waiting for the elevation of the temperature of the gas sensor 101, conducts measurement at high accuracy. Then, the heater 103 is turned OFF and the measured data is sent to the server 1. The server 1 judges that the sensor node $3_1$ does not detect the leakage based on the measured data and then sends an instruction of turning the heater to ON to the next sensor node $3_2$. Also in the next sensor node $3_2$, same measurement and data sending are conducted, and the server 1 judges that the sensor node $3_2$ does not detect leakage. In the same manner, measurement is conducted in all of the sensor nodes 3.

Figure 8A:
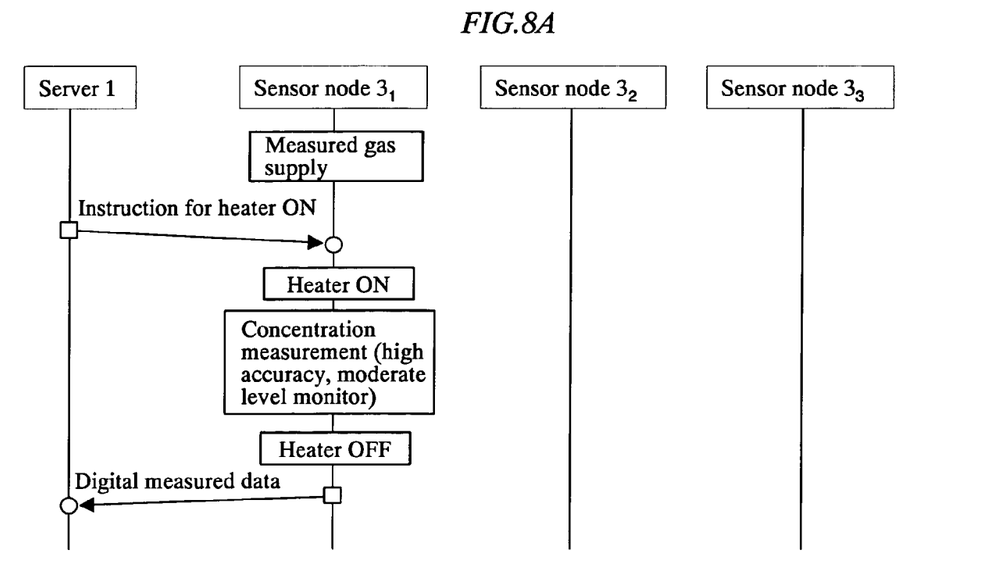
FIG. 8A is a flow in a case of conducting calibration for the measuring performance of the gas sensor.
Figure 8B:
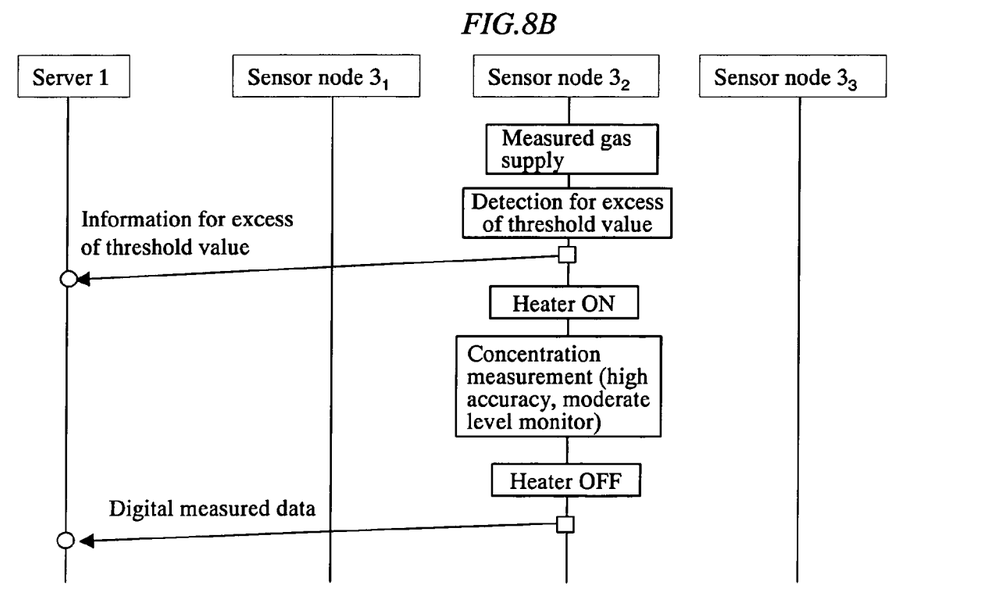
FIG. 8B is a flow in a case of conducting calibration operation for the entire measuring state in a usual case.
Figure 8C:
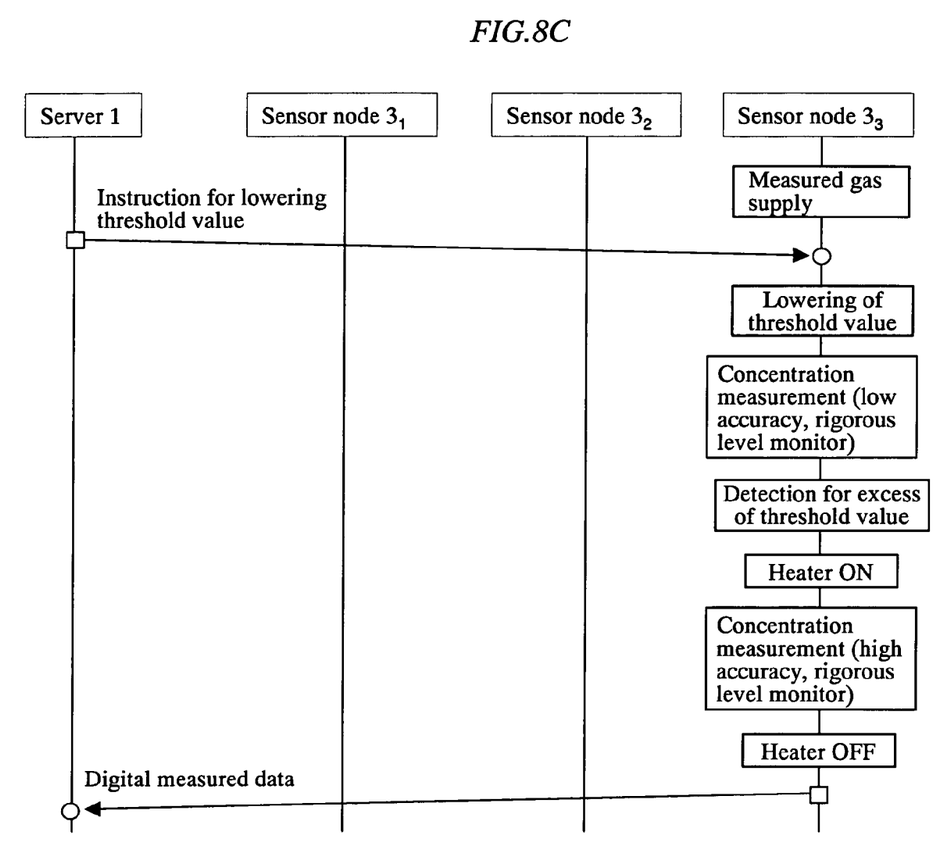
FIG. 8C is a flow in a case of conducting calibration operation for the entire measuring state in a usual case in which a dilution gas the concentration of which does not reach the threshold value is used as a gas to be detected.

FIG. 8A to FIG. 8 are, respectively, views for explaining the flow of calibration. The calibration is a procedure of confirming the operation of each sensor node, for example, by flowing a target gas, a diluted target gas or a simulation gas when the detection system is at first installed in the site or upon periodical inspection conducted, for example, about once per one-half year. As the procedure, three types are illustrated in FIG. 8A to FIG. 8C. In any case, operators located at the server 1 and the sensor node 3 take communication with each other and a gas to be detected by the gas sensor 101 is supplied.

FIG. 8A is a flow in a case of the calibrating operation for the measurement performance of the gas sensor. Like the periodical measurement, the server 1 instructs heater to ON to all of the sensor nodes $3_1$ in a state where the gas to be detected is supplied, and the sensor node $3_1$ sends measured data at high accuracy for the gas concentration to the server 1. While the calibrating operation is conducted successively for other sensor node $3_2$, sensor node $3_3$, etc, this is not illustrated.

FIG. 8B is a flow in a case of the calibrating operation for entire usual measured state. In a case where the gas to be detected is not dangerous, since long time flow of gas causes no problems, the detection flow of the sensor node $3_1$ explained for FIG. 4A may be taken. In this calibration however, it is not necessary to send the instruction of lowering the threshold value to other sensor nodes. FIG. 8B shows an example of conducting calibration between the server 1 and the sensor node $3_2$. This is conducted successively also for other sensor nodes 3.

FIG. 8C shows another flow of conducting calibrating operation for entire usual measurement state, which is the case of using a diluted gas the concentration of which does not reach the threshold value as other gas to be detected. In this case, lowering of the threshold value is previously instructed from the server 1 to the sensor node to check the response of the sensor node. Even when the concentration of the gas to be detected is not at such a level as reaching the threshold value, the sensor node detects the gas by the lowering of the threshold value, turns the heater 103 to ON to switch to measurement to that at high accuracy and sends the measured data for the gas concentration to the server 1. FIG. 8C shows an example of conducting the calibrating processing between the server 1 and the sensor node $3_2$. This is to be conducted successively also for other sensor nodes 3.

While explanation has been made that the calibrating operation is to be conducted successively for each sensor node 3, it will be apparent that the calibrating operation may be conducted collectively for all the sensor nodes 3.

According to this embodiment, since the ON time for the heater can be decreased as short as possible, each of the gas sensors can be driven, for example, by dry cells, which provides advantageous effects of increasing the degree of freedom for the arrangement of the gas sensors and facilitating the maintenance of the system.

In the foregoing embodiments, while the standard concentration value stored in the controller of the sensor node and the measured concentration data are compared with respect to the excess of threshold value or the judgment for leakage, it will be apparent that the system may also be constituted by providing such function to the server, collectively analyzing the information for the measured concentration of each sensor node on the side of the server, and taking adequate action such as indication of leakage level, issue of alarm or shutting of gas. Further, while the heater is turned ON only during measurement at high accuracy such that the ON time of the heater is decreased as short as possible, in a case where a sufficient power supply is available, it may be adapted to continue the measurement at high accuracy and data sending till the server sends the information depending on the result of collective judgment, so that the server can judge corresponding to the change of the state.

According to the present invention, power supply to the heater can be minimized and the amount of the power consumption can be saved greatly.

What is claimed is:

1. A gas detection system comprising a plurality of sensor nodes located dispersedly, each having a gas sensor module and a communication control module having a controller connected with the gas sensor module and a communication system, and a server associated with each of the plural sensor nodes and sending a control signal to necessary sensor nodes, wherein each of the gas sensor module has a gas sensor, a temperature control device for the gas sensor and a temperature measuring device for the gas sensor, wherein the controller, upon detecting that the measured value of the gas sensor exceeds a predetermined threshold value, operates the temperature control device to increase the measuring accuracy of the gas sensor and informs that the measured value of the gas sensor exceeds a predetermined threshold value by way of the communication control module to the server, in the server, a definition of a sensor node in the vicinity to each of the plurality of sensor nodes is registered respectively, and the server, upon receiving the information that the measured value of the gas sensor of any one of said sensor nodes exceeds the predetermined threshold value sends a control signal for lowering the threshold value relative to the measured value of the gas sensor to each of the other corresponding sensor nodes in the vicinity.

2. The gas detection system according to claim 1, wherein the server sends a signal to the sensor nodes for operating the temperature control devices of the gas sensors in a state of supplying a predetermined gas to the gas sensors on a predetermined period or at a desired timing.

3. The gas detection system according to claim 1, wherein the server supplies a predetermined gas to the gas sensors on a predetermined period or at a desired timing.

4. The gas detection system according to claim 1, wherein the server sends an instruction to the sensor node for lowering the threshold value of the gas sensors in a state of supplying a predetermined gas to the gas sensors on a predetermined period or at a desired timing.

5. The gas detection system according to claim 1, wherein the sensor node, comprising:

a gas sensor for measuring the gas concentration;

a threshold value setting circuit for storing a predetermined threshold value; and a comparator for comparing the gas concentration with the predetermined threshold value, wherein the threshold value setting circuit lowers the stored threshold value to less than the predetermined threshold value based on the output from the comparator or the instruction from the outside.

* * * * *